US012569580B2

(12) United States Patent
Choi

(10) Patent No.: US 12,569,580 B2
(45) Date of Patent: Mar. 10, 2026

(54) UV STEAM STERILIZER

(71) Applicant: Haenim Co., Ltd., Incheon (KR)

(72) Inventor: Heung Bae Choi, Incheon (KR)

(73) Assignee: Haenim Co., Ltd., Incheon (KR)

( * ) Notice: Subject to any disclaimer, the term of this patent is extended or adjusted under 35 U.S.C. 154(b) by 477 days.

(21) Appl. No.: 18/170,328

(22) Filed: Feb. 16, 2023

(65) Prior Publication Data

US 2024/0050604 A1 Feb. 15, 2024

(30) Foreign Application Priority Data

Aug. 12, 2022 (KR) ......................... 10-2022-0101018

(51) Int. Cl.
*A61L 2/10* (2006.01)
*A61L 2/07* (2006.01)
(52) U.S. Cl.
CPC *A61L 2/10* (2013.01); *A61L 2/07* (2013.01); *A61L 2202/11* (2013.01)
(58) Field of Classification Search
CPC ..... A61L 2/07; A61L 2/10; A61L 2/24; A61L 2/26; A61L 2202/11; A61L 2202/122; A61L 2202/14; C02F 1/32; C02F 2303/04; F26B 21/001
See application file for complete search history.

(56) References Cited

FOREIGN PATENT DOCUMENTS

| | | | | | |
|---|---|---|---|---|---|
| CN | 105435254 A | * | 3/2016 | | |
| KR | 10-2007-0115148 | | 5/2006 | | |
| KR | 10-0883689 | | 1/2009 | | |
| KR | 20090083088 A | * | 8/2009 | ............... | A61L 2/26 |
| KR | 10-1906230 | | 10/2018 | | |
| KR | 10-2019-0109938 | | 9/2019 | | |

* cited by examiner

*Primary Examiner* — Jennifer Wecker
*Assistant Examiner* — Brady C Pilsbury
(74) *Attorney, Agent, or Firm* — Yancy IP Law, PLLC

(57) ABSTRACT

There is provided a UV steam sterilizer including, a main body provided to generate steam by heating water, and a to-be-sterilized-article container having a space containing the to-be-sterilized-article to be sterilized by the steam and detachably placed on the main body. In addition, the UV steam sterilizer includes, a heating plate, heating the water contained in a water containing groove, installed at the bottom of the water containing groove provided on the upper surface of the main body in a form of being concave downward, a water level sensor installed on a sidewall of the water containing groove to detect the lowest water level of the water contained in the water containing groove, a steam heater built in the main body to control to heat the heating plate during operation and to stop when the water level sensor detects the lowest water level, and a UV irradiation unit installed on the heating plate to irradiate ultraviolet rays to residual water remaining in the water containing groove while maintaining the lowest water level as the water level, and controlled to irradiate the ultraviolet rays after the steam heater stops.

10 Claims, 6 Drawing Sheets

UV STEAM STERILIZER

CROSS-REFERENCE TO RELATED APPLICATIONS

This application claims the priority of Korean Patent Application No. 10-2022-0101018 filed on Aug. 12, 2022, in the Korean Intellectual Property Office, the disclosure of which is incorporated herein by reference.

BACKGROUND OF THE INVENTION

Field of the Invention

The present disclosure relates to a steam sterilizer for sterilizing baby products with steam, and more particularly, to a UV steam sterilizer provided to leave residual water on a heating plate after steam sterilization is completed and sterilize the residual water with ultraviolet rays.

Description of the Related Art

An ultraviolet (UV) sterilizer, a steam sterilizer, etc. are known as sterilizers for sterilizing baby products such as baby bottles, teats, and teethers. The UV sterilizer is configured to sterilize baby products by irradiating ultraviolet rays on the washed baby products, and the steam sterilizer is configured to sterilize the washed baby products with steam generated when water is heated.

The UV sterilizer is disclosed in Korean Patent No. 10-1906230 (A nursing bottle sterilization) and Korean Patent Application Publication No. 10-2019-0109938 (Electric sterilizer). In the nursing bottle sterilizer of the above Korean Patent, an ultraviolet lamp is installed on the ceiling of a housing prepared to accommodate a baby bottle, and while the ultraviolet lamp rotates, ultraviolet rays are irradiated to the baby bottle. In the electric sterilizer of the above Korean Patent Application Publication, an ultraviolet irradiator for irradiating ultraviolet rays with a baby bottle is installed on both the ceiling and the floor of the housing.

On the other hand, Korean Patent Application Publication No. 10-2007-0115148 (A nursing bottle sterilization) and Korean Patent No. 10-0883689 (Sterilizer for nursing bottle) disclose the above steam sterilizer. The nursing bottle sterilizer disclosed in Korean Patent Application Publication No. 10-2007-0115148 has a collecting cup to collect the liquid falling from the nursing bottle in a washed state, eliminating the hassle of cleaning the heating plate soiled by the liquid. The nursing bottle sterilizer disclosed in the Korean Patent No. 10-0883689 discloses a technique of drying the nursing bottle with hot air after steam sterilization is completed.

Patent Document

Korean Patent No. 10-1906230 (A nursing bottle sterilization)
Korean Patent Publication No. 10-2019-0109938 (Electric sterilizer)
Korean Patent Publication No. 10-2007-0115148 (A nursing bottle sterilization)
Korean Patent No. 10-0883689 (Sterilizer for nursing bottle)

SUMMARY OF THE INVENTION

A steam sterilizer is generally configured to operate a heater that heats a heating plate until all the water on the heating plate evaporates. In addition, in such a steam sterilizer, since it is impossible to detect the exact time when all the water evaporates, the heater is usually operated even after all the water has evaporated. However, if the heater is operated in a state where there is no water on the heating plate, the heater is overloaded, and if this phenomenon is repeated, the life-span of the heater is shortened.

On the other hand, since a user sterilizes a plurality of baby bottles and a plurality of teats at once with one steam sterilization, and then takes them out one by one whenever necessary, the already sterilized baby bottles and teats are stored in the steam sterilizer for a long time. In addition, if there is residual water on the heating plate after the steam sterilization is completed, a space where the bottles and teats are stored is also contaminated, because the residual water is contaminated with germs for a long time while the already sterilized bottles and teats are stored. In addition, an unsanitary problem also arises in that contaminated residual water is used for the next steam sterilization. In particular, baby bottles and teats are washed with detergent and water and then sterilized with steam, and if the cleaning is not done properly, liquids including powdered milk or breast milk fall from the bottles and teats onto the heating plate, so bacteria contamination in the residual water above is intensified. For this reason, attempts to prevent overload of the heater by leaving water on the heating plate after steam sterilization is completed has not been made until now.

Therefore, an aspect of the present disclosure provides a technology capable of preventing contamination of the residual water while preventing overload of the heater by leaving residual water on the heating plate after steam sterilization is completed.

According to an aspect of the present disclosure, provided is a UV steam sterilizer including: a main body provided to generate steam by heating water; and a to-be-sterilized-article container having a space containing the to-be-sterilized-article to be sterilized by the steam and detachably placed on the main body. In addition, the UV steam sterilizer includes: a heating plate, heating the water contained in a water containing groove, installed at the bottom of the water containing groove provided on the upper surface of the main body in a form of being concave downward; a water level sensor installed on a sidewall of the water containing groove to detect the lowest water level of the water contained in the water containing groove; a steam heater built in the main body to control to heat the heating plate during operation and to stop when the water level sensor detects the lowest water level; and a UV irradiation unit installed on the heating plate to irradiate ultraviolet rays to residual water remaining in the water containing groove while maintaining the lowest water level as the water level, and controlled to irradiate the ultraviolet rays after the steam heater stops.

The UV irradiation unit includes a watertight body installed in an installation hole formed in the heating plate to be watertight; a light transmitting cap penetrating the watertight body while being tightly inserted into the watertight body, made of a material through which the ultraviolet rays transmit, and having an upper surface exposed to the water containing groove; a bracket including a support member located inside the main body and contacting a lower end of the watertight body and a lower end of the light transmitting cap, and a protruding member provided to protrude upward of the support member and inserted into the light transmitting cap; and a printed circuit board fixed onto the upper surface of the protruding member and mounted with a UV LED. An O-ring is interposed between an inner surface of the light transmitting cap and an outer surface of the protruding member.

The to-be-sterilized-article container includes a hollow housing forming a side wall of the containing space; a bottom plate detachably coupled to the hollow housing and forming the bottom of the containing space, and supporting the to-be-sterilized-article and having steam passage holes for passage of the steam; and a magnet installed on the bottom plate. In addition, when the hollow housing coupled to the bottom plate is placed in the main body, a hall sensor detecting the magnet is installed in the main body. The UV irradiation unit is controlled to irradiate the ultraviolet rays only when the hall sensor detects the magnet.

The UV steam sterilizer includes a drying module built in the main body, and provided to form hot air by heating outside air during operation, and then to blow the hot air to the containing space, and controlled to operate immediately after the steam heater stops.

The drying module is controlled to operate for a preset operation time periodically when there is an input of a user for notifying that the to-be-sterilized-article sterilized with the steam is present in the containing space. In addition, the UV steam sterilizer unit may be controlled to irradiate the ultraviolet rays when the drying module operates.

The drying module includes a duct having an outside air inlet for introducing the outside air and a hot air outlet for discharging the hot air upward; a fan and a hot air heater installed inside the duct; and a door installed in the hot air outlet to be opened by a wind pressure of the hot air and closed by its own weight. In addition, a hood for guiding the hot air which flows out from the hot air outlet is provided on the upper surface of the main body while limiting an opening angle of the door to an acute angle.

A bottom portion of the duct located below the hot air outlet is constituted by a water collection groove formed more concavely downward than a bottom portion of the duct where the fan and the hot air heater are located. At this time, a duct drain hole is formed at the bottom of the water collection groove, and the duct drain hole communicates with a main body drain hole formed at the bottom of the main body.

According to exemplary embodiments of the present disclosure, since the residual water remains on the heating plate at the end of the steam sterilization, the problem of overloading the steam heater does not occur, and contamination of the residual water is prevented because the residual water is sterilized with ultraviolet rays.

In addition, according to the exemplary embodiments of the present disclosure, since the UV irradiation unit is detachably installed in the installation hole of the heating plate, maintenance of the UV irradiation unit is easy, and since the UV irradiation unit includes a watertight body, watertightness may be achieved in the installation hole of the heating plate.

In addition, according to the exemplary embodiments of the present disclosure, the printed circuit board and the UV LED of the UV irradiation unit may be positioned in a more reliable watertight space due to the O-ring.

In addition, according to the exemplary embodiments of the present disclosure, since ultraviolet rays are irradiated only when the bottom plate of the container for the sterilized article covers the UV irradiation unit, there is no problem in that the user's body is exposed to ultraviolet rays emitted from the UV irradiation unit.

In addition, according to the exemplary embodiments of the present disclosure, the sterilized article with steam may be dried with hot air formed by the drying module.

In addition, according to the exemplary embodiments of the present disclosure, the user may be provided with the convenience of simultaneously operating the drying module and the UV irradiation unit.

In addition, according to the exemplary embodiments of the present disclosure, an unintended problem in which water in the water containing groove flows into the fan and the hot air heater of the drying module may be surely prevented.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE PREFERRED EMBODIMENT

Hereinafter, exemplary embodiments of a UV steam sterilizer according to the present disclosure will be described in detail with reference to the accompanying drawings. Terms or words used below should not be interpreted as typical or dictionary meanings, but should be interpreted as having meanings and concepts which comply with the technical spirit of the present disclosure, based on the principle that an inventor may appropriately define the concept of the term to describe his/her own disclosure in the best method.

Figure 1:
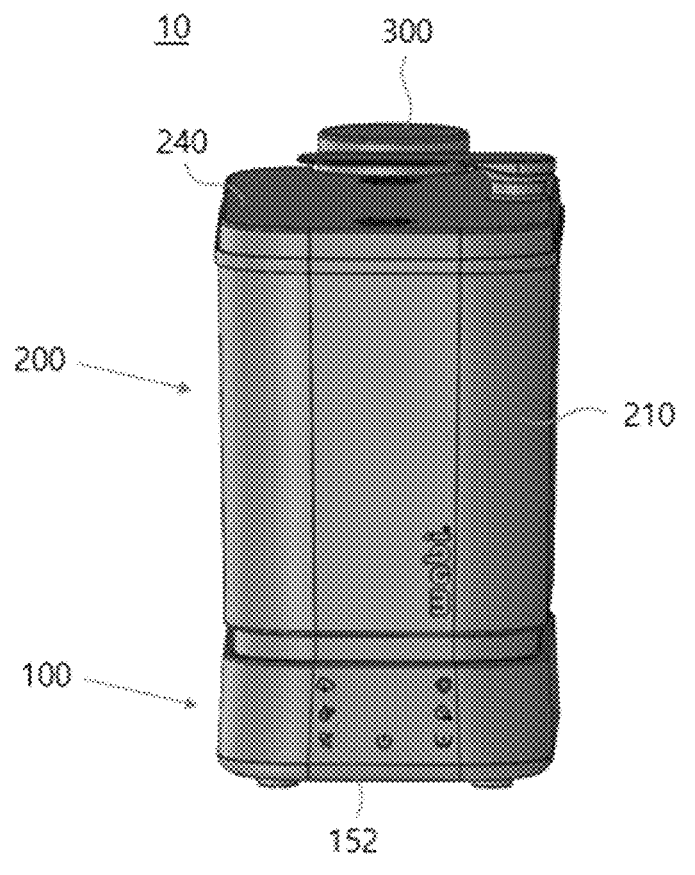
FIG. 1 is a perspective view illustrating a UV steam sterilizer according to the present disclosure.

As illustrated in FIG. 1, a UV steam sterilizer 10 according to the present disclosure includes a main body 100, a to-be-sterilized-article container 200, and a water container 300. The main body 100 is provided to generate steam by heating water. The to-be-sterilized-article container 200 has a containing space (not illustrated) in which to-be-sterilized-articles (not illustrated) such as baby articles (baby bottles, teats, teethers, etc.) are contained, and is detachably placed on the main body 100. The water container 300 stores water to be steamed and is detachably coupled to the main body 100. Hereinafter, the main body 100, the to-be-sterilized-article container 200, and the water container 300 will be described.

<Main Body 100>

Figure 2:
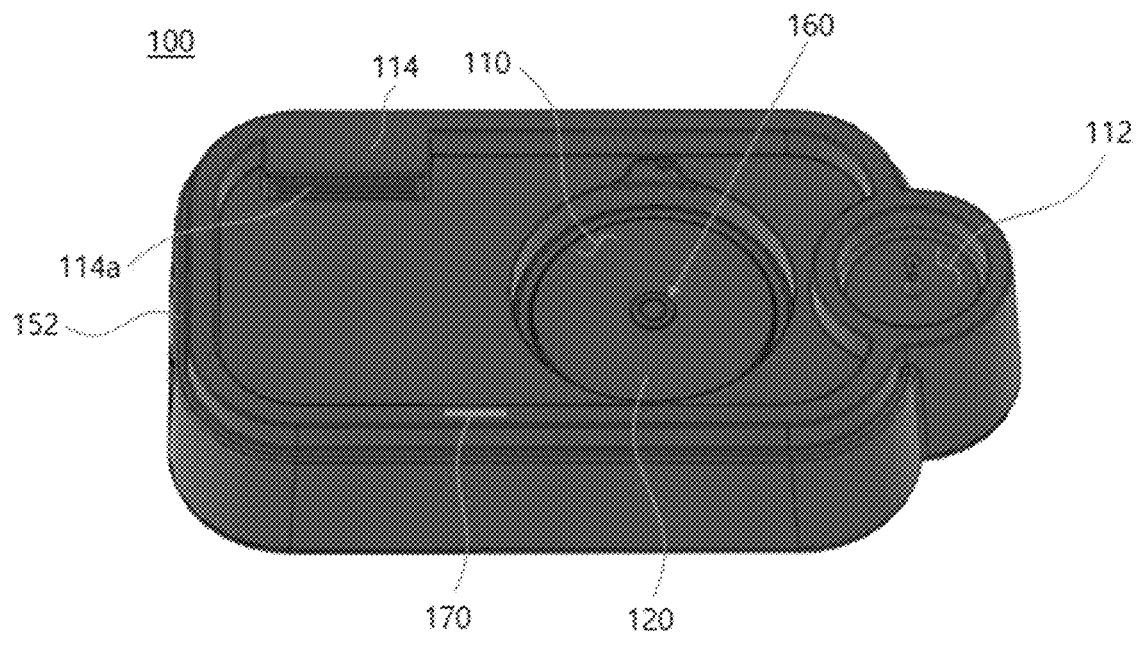
FIG. 2 is a perspective view of a main body illustrated in FIG. 1.
Figure 3:
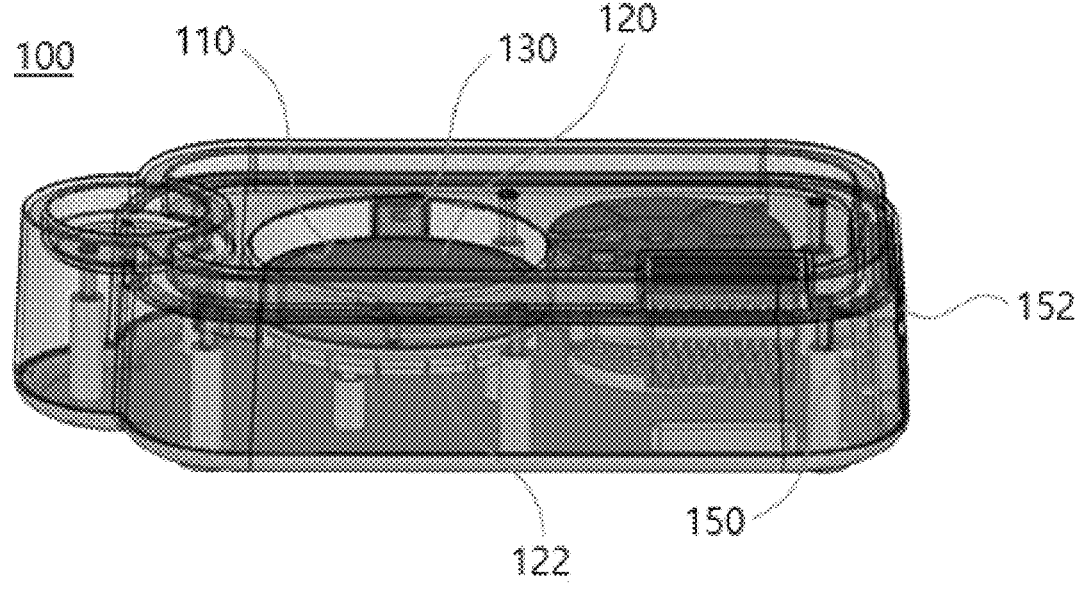
FIG. 3 is a projection view of the main body illustrated in FIG. 2.

As illustrated in FIG. 2, a concave water containing groove 110 is formed on the upper surface of the main body 100, and water to be heated by steam is contained in the water containing groove 110. In addition, a heating plate 120 for heating water is installed at the bottom of the water containing groove 110 to be watertight. As illustrated in FIG. 3, the main body 100 has a built-in steam heater 122, and when the steam heater 122 operates, the heating plate 120 is heated, and then the water contained in the water containing groove 110 is heated and turns into steam.

As illustrated in FIG. 3, a water level sensor 130 for detecting the lowest water level of the water contained in the water containing groove 110 is installed on the side wall of the water containing groove 110. When the water is turned into steam by operating the steam heater 122 when the water is filled to the full water level in the water containing groove 110, the water level of the water filled in the water containing groove 110 is gradually lowered, and then when the water level reaches the water level sensor 130, the water level sensor 130 outputs the lowest water level detection signal to a control unit 150 constituted by the printed circuit board. Further, the control unit 150 stops the steam heater 122 upon receiving the lowest water level detection signal.

Therefore, in the UV steam sterilizer 10 according to the present disclosure, when the process of heating water to steam is completed, residual water having the lowest water level as the water level remains in the water containing groove 110, and thus, even though there is no water in the water containing groove 110, the steam heater 122 operates so that the problem of overloading the steam heater 122 does not occur.

On the other hand, if the state in which residual water remains in the water containing groove 110 continues, the residual water may be contaminated due to bacterial propagation. Therefore, in the ultraviolet steam sterilizer according to the present disclosure, a UV irradiation unit 160 for sterilizing the residual water is provided.

Figure 4:
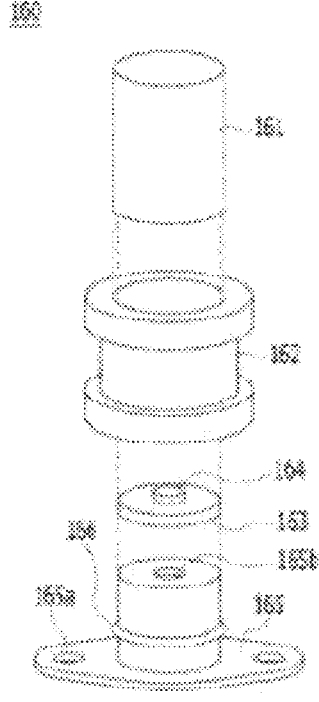
FIG. 4 is an exploded perspective view of a UV irradiation unit illustrated in FIG. 2.
Figure 5:
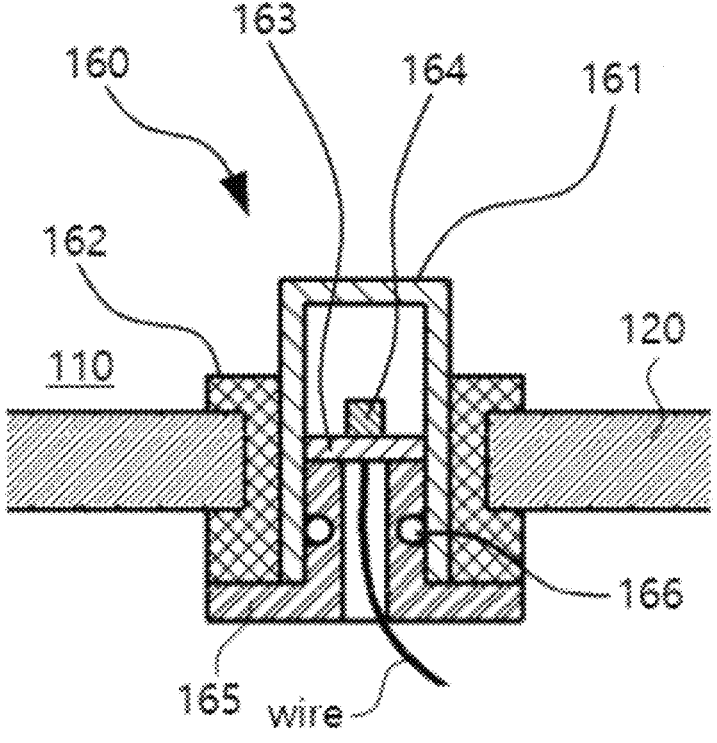
FIG. 5 is a cross-sectional view of the UV irradiation unit illustrated in FIG. 2.

The UV irradiation unit 160 is installed in the center portion of the heating plate 120 as illustrated in FIG. 2, and includes a watertight body 162, a light transmitting cap 161, a bracket 165 and a printed circuit board 163 as illustrated in FIGS. 4 and 5.

The light transmitting cap 161 has a hollow cap shape and is made of a material (e.g., quartz glass, etc.) capable of transmitting ultraviolet rays.

The bracket 165 includes a flat plate-shaped support member and a protruding member protruding upward from approximately the center of the support member. A pair of bolt holes 165a are formed in the support member. And the protruding member has a hollow.

The printed circuit board 163 is fixed to the upper surface of the protruding member of the bracket 165 with an adhesive. In addition, a UV LED 164 is mounted on the printed circuit board 163. Power supplied to the main body 100 is supplied to the printed circuit board 163 through wires, and then the UV LED 164 operates to irradiate ultraviolet rays.

If the protruding member is inserted into the light transmitting cap 161 until the support member contacts the lower end of the light transmitting cap 161, the bracket 165 to which the printed circuit board 163 is fixed is coupled to the light transmitting cap 161. And when the bracket 165 and the light transmitting cap 161 are coupled in this way, the printed circuit board 163 and the UV LED 164 are located inside the light transmitting cap 161. Accordingly, the ultraviolet ray irradiated from the UV LED 164 transmits light through the light transmitting cap 161. Meanwhile, an O-ring 166 is interposed between the outer surface of the protruding member and the inner surface of the light transmitting cap 161 to seal the printed circuit board 163 and the UV LED 164 watertightly.

The watertight body 162 is installed in the form of being inserted into the installation hole of the heating plate 120, but is installed so as to be caught on the upper and lower surfaces of the heating plate 120. And the watertight body 162 has the hollow. The watertight body 162 is made of a material such as heat-resistant silicone or heat-resistant rubber so as to be watertight in the installation hole of the heating plate 120 and to withstand a heating temperature of the heating plate 120.

In a state where the bracket 165 and the light transmitting cap 161 are coupled and the watertight body 162 is installed in the installation hole of the heating plate 120, when the light transmitting cap 161 penetrates the watertight body 162 while being tightly clamped in the hollow of the watertight body 162 until the support member of the bracket 164 contacts the lower end of the watertight body 162, and then a bolt (not illustrated) passed through a bolt hole 165a of the support member is fastened to a bolt fastening member (not illustrated) formed on the lower surface of the heating plate 120, the UV irradiation unit 160 is detachably installed on the heating plate 120.

And when the UV irradiation unit 160 is installed as above, the upper surface of the light transmitting cap 161 is exposed to the water containing groove 110 as illustrated in FIGS. 2 and 5, and the ultraviolet rays transmitted through the light transmitting cap 161 are irradiated to the residual water of the water containing groove 110, and thus, the residual water is sterilized by ultraviolet rays to prevent contamination of the residual water.

The UV irradiation unit 160 described above is for sterilization of the residual water, and the control unit 150 operates the UV irradiation unit 160 only in a state in which the steam heater 122 is stopped. At this time, the control unit 150 may control the UV irradiation unit 160 according to a preset control method. For example, the control unit 150 operates the UV irradiation unit 160 for a preset operating time (e.g., about 30 minutes to 1 hour) immediately after stopping the steam heater 122, and then operates the UV irradiation unit 160 every preset period (e.g., every 1 hour) during the above operation time.

Due to the UV irradiation unit 160, in the UV steam sterilizer 10 according to the present disclosure, contamination of the residual water remaining in the water containing groove 110 may be prevented.

On the other hand, a drying module for drying the sterilized by steam may be built into the main body 100. In addition, the drying module may include a duct 140, a door 142, a fan 144, and a hot air heater 146. Hereinafter, the drying module will be described with reference to FIGS. 6 to 9.

Figure 7:
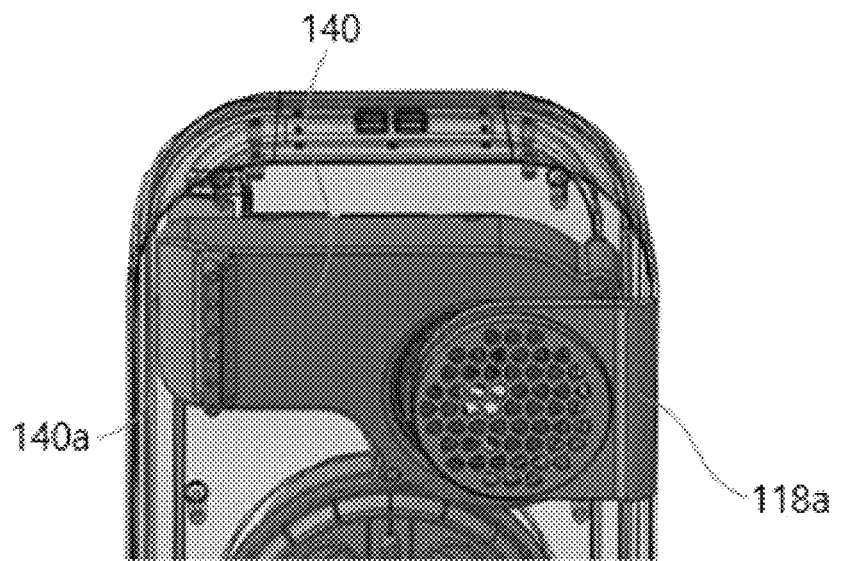
FIG. 7 is a perspective view of the duct illustrated in FIG. 6 viewed from the bottom.
Figure 9:
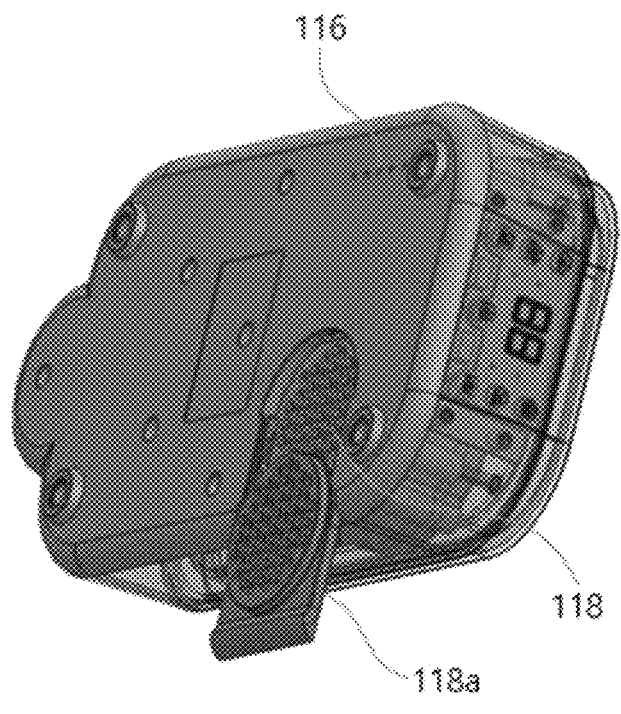
FIG. 9 is a perspective view of the main body illustrated in FIG. 1 viewed from the bottom.

The duct 140 has an outside air inlet at the bottom for introducing outside air from the main body 100 (see FIG. 7). In addition, outside air inlet holes 118 are provided at the bottom of the main body 100 as illustrated in FIG. 9. The outside air introduced into the main body 100 through the outside air inlet holes 118 may flow into the duct 140 through the outside air inlet. At this time, as illustrated in FIG. 9, a filter plate 118a may be coupled to the bottom of the main body 100 where the outside air inlet holes 118 are located, in a sliding manner, and when the outside air passes through the filter plate 118a, foreign substances included in the outside air may be filtered by the filter plate 118a.

Figure 6:
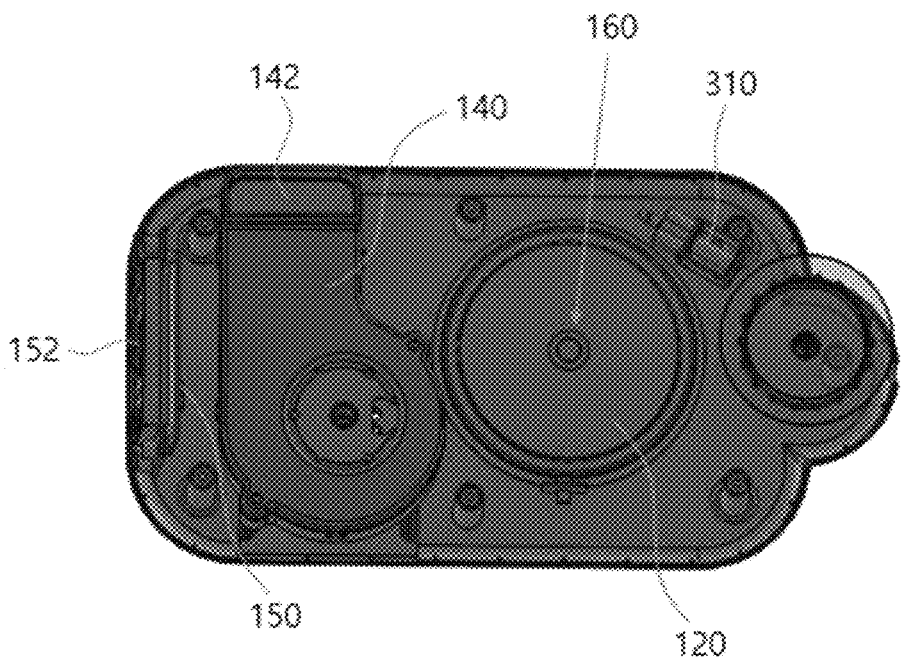
FIG. 6 is a perspective view of a duct built into the main body illustrated in FIG. 2 viewed from the top.

The duct 140 has a hot air outlet on the upper surface for discharging hot air upward (see FIG. 6). And, as illustrated in FIG. 2, a hood 114 having an outlet 114a is provided on the upper surface of the main body 110 so as to protrude upward. The hot air discharged through the hot air outlet may flow into the upper space of the upper surface of the main body 110 through the hood 114.

Figure 8:
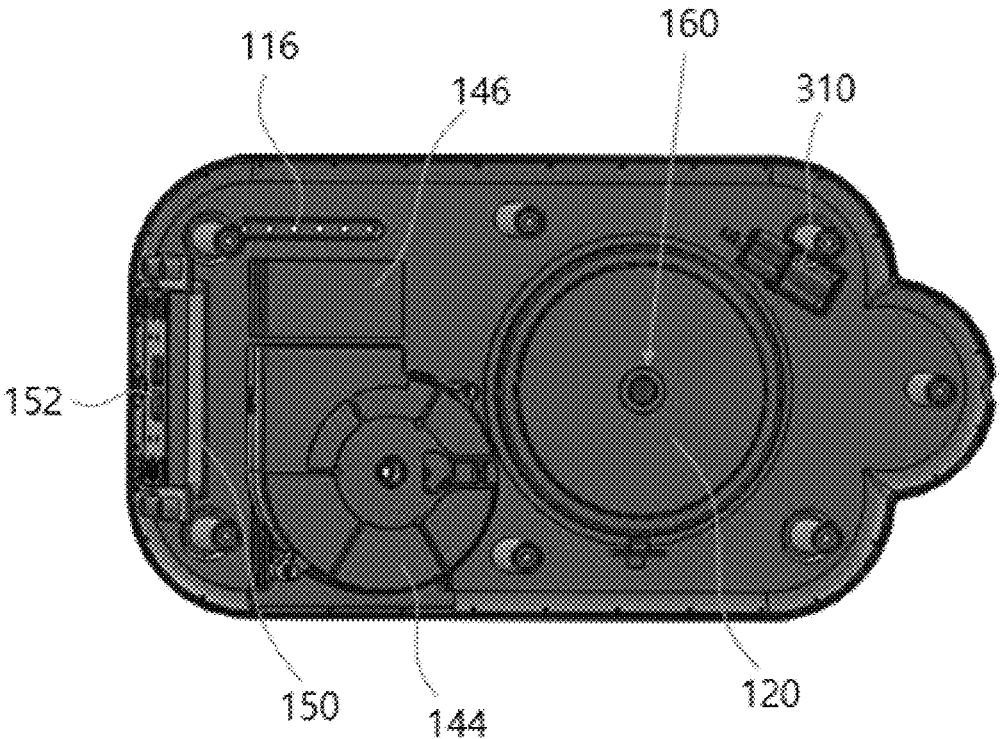
FIG. 8 is a perspective view illustrating a state in which the duct is omitted in FIG. 6.

As illustrated in FIG. 8, the fan 144 and the hot air heater 146 are built into the duct 140 described above. When the fan 144 and the hot air heater 146 operate, the outside air flows along the duct 140 and is heated with the hot air by the hot air heater 146, and the hot air flows into the upper space of the upper surface of the main body 100 through the hot air outlet of the duct 140 and an outlet 114a of the hood 114.

The door 142 is installed at the hot air outlet to open and close in a casement manner as illustrated in FIG. 6. Based on FIG. 6, the upper end of the door 142 is a fixed end that rotates in a hinged manner, and the lower end of the door 142 is a free end. The hot air flows out from the hot air outlet while opening the door 142 with air pressure, and when there is no outflow of the hot air, the door 142 is closed by its own weight. In this case, since the door 142 may not be closed by its own weight when the opening angle of the door 142 is an obtuse angle, it is preferable that the hood 114 is provided to limit the opening angle of the door 142 to an acute angle.

Even if the door 142 is not installed at the hot air outlet of the duct 142, there is no problem in supplying the hot air to the upper space of the upper surface of the main body 100. However, if a situation in which water in the water containing groove 110 flows into the duct 140 through the hood 114 unintentionally occurs, the fan 144 and the hot air heater 146 may be out of order, so it is recommended to install the door 142 to prevent water from entering the duct 140.

As illustrated in FIG. 7, a water collection groove having duct drain holes 140a may be provided at the bottom of the duct 140. In this case, the water collection groove is located below the hot air outlet, and is provided in a more concave shape downward than the bottom portion of the duct 140 where the fan 144 and the hot air heater 146 are located. And, as illustrated in FIGS. 8 and 9, main body drain holes 116 communicating with the duct drain holes 140a are provided at the bottom of the main body 100.

The door 142 is installed to prevent the water in the water containing groove 110 from unintentionally flowing into the duct 140, but even in this case, the possibility of water flowing into the duct 140 is not completely excluded. Therefore, when water flows into the duct 140 even though there is the door 142, it is preferable to more reliably protect the fan 144 and the hot air heater 146 by collecting the water into the water collection groove and then draining the water through the drain holes 116 and 140a.

The drying module as described above is for drying the to-be-sterilized-articles that have been sterilized with steam, and the control unit 150 operates the drying module only in a state in which the steam heater 122 is stopped. At this time, the control unit 150 may control the drying module according to a preset control method. For example, the control unit 150 stops the steam heater 122 and immediately operates the drying module, that is, the fan 144 and the hot air heater 146, for a preset operating time (e.g., about 30 minutes to 1 hour), and then, if there is a user's input indicating that the to-be-sterilized-article is in the to-be-sterilized-article container 200, the drying module is operated for the operating time at a preset cycle (e.g., every hour).

As illustrated in FIG. 1, a control panel 152 including input buttons for receiving various commands from the user (e.g., an on/off button for an on/off command, a sterilization button for starting steam sterilization, a storage button for a storage command for a steam sterilized article, and a temperature setting button for setting a hot air temperature) and a display for displaying states of the steam sterilizer 10 (an on/off state, a sterilization state, a storage state, and a hot air temperature) is installed in the main body 100. Further, the user may perform an input notifying that the steam sterilized article is in the to-be-sterilized-article container 200 by selecting the storage button.

When the drying module is provided, the control unit 150 may synchronize the operation of the drying module and the operation of the UV irradiation unit 160. That is, the control unit 150 may also operate the UV irradiation unit 160 upon operating the drying module, and may also stop the UV irradiation unit 160 upon stopping the drying module. In this case, the user may be provided with the convenience that the drying module and the UV irradiation unit 160 may be operated at the same time only by selecting the storage button.

On the other hand, a hall sensor 170 for sensing magnetic force may be provided on the upper surface of the main body 100 as illustrated in FIG. 2. In this case, the control unit 150 operates the UV irradiation unit 160 only when the hall sensor 170 outputs a magnetic detection signal.

<To-be-Sterilized-Article Container 200>

Figure 10:
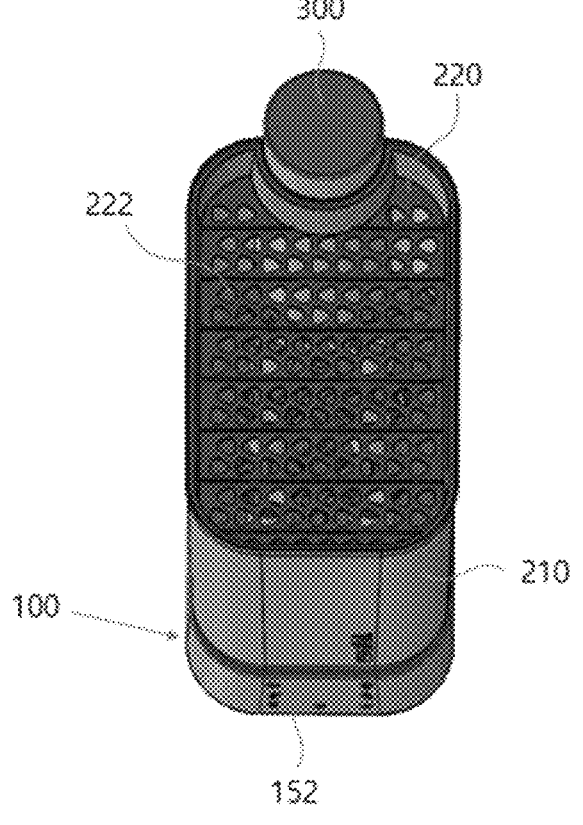
FIG. 10 is a perspective view illustrating an open state of a cover in FIG. 1.
Figure 11:
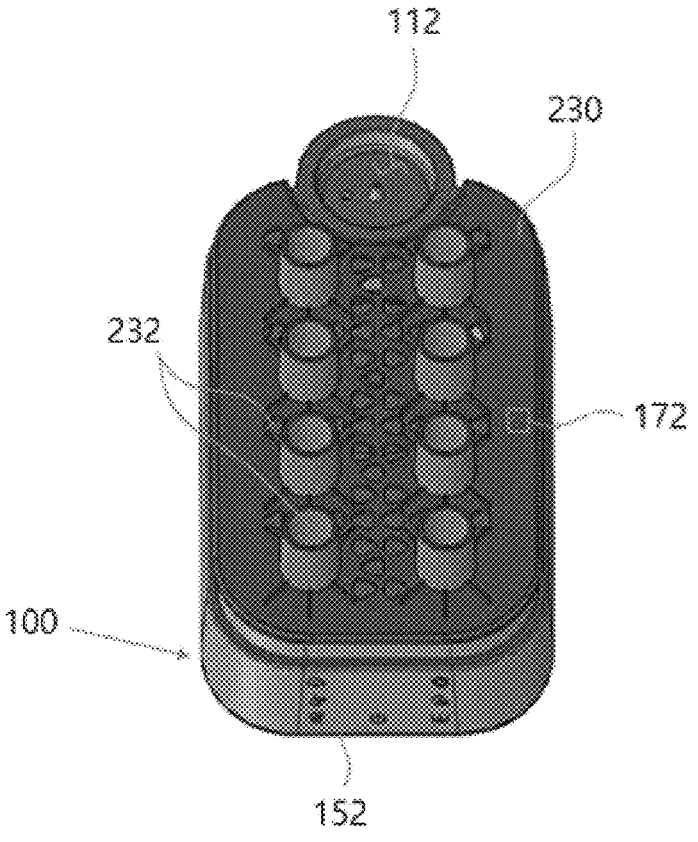
FIG. 11 is a perspective view illustrating a state in which sidewalls are omitted in FIG. 10.

As illustrated in FIGS. 1, 10 and 11, the to-be-sterilized-article container 200 may include a hollow housing 210, a bottom plate 230, a cover 240, and an upper support plate 220.

The hollow housing 210 forms a side wall of a containing space (not illustrated) in which the to-be-sterilized-article is contained, and top and bottom surfaces of the hollow housing 210 are configured as open surfaces. The hollow housing 210 is detachably placed on the upper surface of the main body 100.

The bottom plate 230 forms the bottom of the containing space. In addition, the bottom plate 230 is coupled to the hollow housing 210 to allow entering or exiting the open top surface of the hollow housing 210, but not entering or exiting the open bottom surface of the hollow housing 210. As illustrated in FIG. 11, a plurality of protrusions inserted into the inlet of the inverted baby bottle are provided on the bottom plate 230, and steam passage holes 232 are provided at the protrusions and around the protrusions. Accordingly, steam generated when heating water in the water containing groove 110 passes through the steam passage holes 232 and sterilizes the baby bottles placed on the bottom plate 230. In addition, hot air supplied above the upper surface of the main body 100 also passes through the steam passage holes 232 to dry the steam-sterilized baby bottles.

As illustrated in FIG. 11, a permanent magnet 172 is installed on the lower edge of the bottom plate 230. The permanent magnet 172 is sensed by the hall sensor 170 when the hollow housing 210 coupled to the bottom plate 230 is placed on the main body 100. Further, the control unit 150 operates the UV irradiation unit 160 only when the hall sensor 170 outputs a magnetic force detection signal indicating that the magnetic force of the permanent magnet 172 is detected. Therefore, in the UV steam sterilizer 10 according to the present disclosure, the ultraviolet irradiation unit 160 operates only when the bottom plate 230 is located above the upper surface of the main body 100.

The UV irradiation unit 160 is exposed to the outside as it is when the to-be-sterilized-article container 200 is not placed on the main body 100. In addition, the UV irradiation unit 160 is exposed to the outside when the hollow housing 210 separated from the bottom plate 230 is placed on the main body 100. In addition, when the UV irradiation unit 160 operates in a state in which the UV irradiation unit 160 is exposed to the outside as described above, the user's body is directly exposed to ultraviolet rays irradiated from the UV irradiation unit 160 and is adversely affected. Therefore, as described above, the bottom plate 230 is located on the upper surface of the main body 100 so that the UV irradiation unit 160 may operate only when the UV irradiation unit 160 is covered, so as to certainly prevent the user's body from being directly exposed to ultraviolet rays.

The upper support plate 220 is installed in the form of being placed on top of the hollow housing 210, as illustrated in FIG. 10, and has steam passage holes 222. A teat or teether is placed on the upper support plate 220 to be sterilized and dried by steam and hot air passed through the steam passage holes 222. Meanwhile, as illustrated in FIG. 1, the cover 240 covers the open top surface of the hollow housing 210 to be opened and closed.

<Water tank 300>

Figure 12:
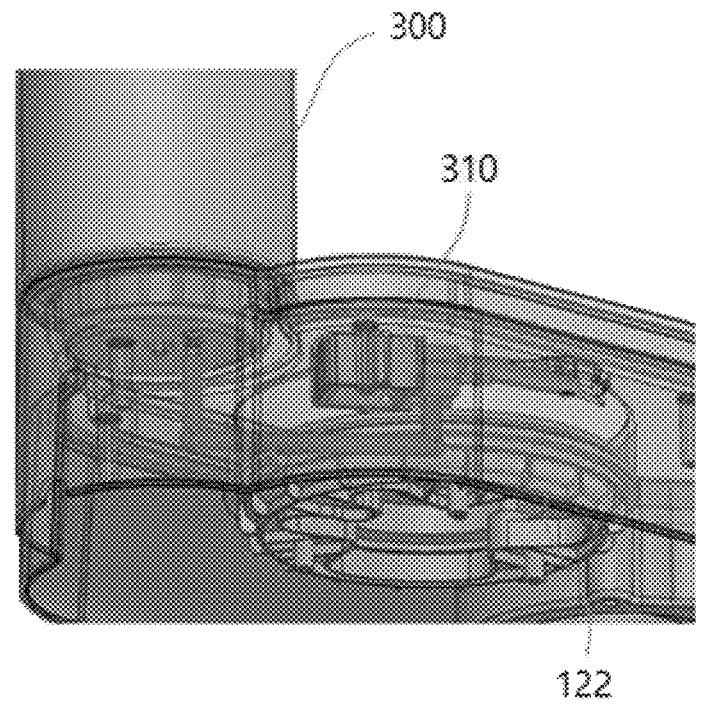
FIG. 12 is a partial projection view of the main body illustrated in FIG. 2.

A water tank seating groove 112 is provided on the upper surface of the main body 100 as illustrated in FIG. 2, and the water tank 300 storing water is placed on the water tank seating groove 112 in an inverted posture as illustrated in FIGS. 1 and 12. In addition, when the water tank 300 is seated on the water tank seating groove 112, water may flow out of the water tank 300.

In addition, a pump 310 is built in the main body 100 as illustrated in FIG. 12, and when the pump 310 operates, water in the water tank 300 is supplied to the water containing groove 110. The control unit 150 controls the pump 310 so that water in the water tank 300 is supplied to the water containing groove 110 by a fixed amount.

When the water tank 300 and the pump 310 are provided, water may be automatically supplied by a fixed amount to the water containing groove 210.

On the other hand, in the UV steam sterilizer 10 according to the present disclosure, the water tank 300 and the pump 310 do not have to be provided, but in this case, the user may manually fill the water containing groove 210 with water.

As described above, although the present disclosure has been described with limited examples and drawings, the present disclosure is not limited thereto, and various modifications and variations may be made within the technical spirit of the present disclosure and the scope of equivalents of the claims to be described below by those skilled in the art to which the present disclosure belongs, and the above-described exemplary embodiments may be variously combined, of course.

What is claimed is:

1. A UV steam sterilizer comprising;
a main body configured to generate steam by heating water;
a container having a containing space for containing an article to be sterilized by the steam, wherein the container is detachably placed on the main body;
a heating plate, for heating water contained in a water containing groove, wherein the heating plate is installed at the bottom of the water containing groove, the water containing groove is provided on an upper surface of the main body, and the water containing groove has a concave downward form;

a water level sensor installed on a sidewall of the water containing groove, wherein the water level sensor is configured to detect when a level of the water contained in the water containing groove is at a lowest level;
a steam heater built in the main body, wherein the steam heater is configured to control heating of the heating plate during operation of the sterilizer, and the steam heater is further configured to stop heating the heating plate when the water level sensor detects the lowest water level; and
a UV irradiation unit installed on the heating plate, wherein the UV irradiation unit is configured to irradiate ultraviolet rays to the water in the water containing groove when the water level is at the lowest water level, and the UV irradiation unit is further configured to irradiate the ultraviolet rays after the steam heater stops.

2. The UV steam sterilizer of claim 1, wherein the UV irradiation unit includes:
a watertight body installed in an installation hole formed in the heating plate to be watertight;
a light transmitting cap penetrating the watertight body while being tightly inserted into the watertight body, the light transmitting cap being made of a material through which the ultraviolet rays transmit, and the light transmitting cap having an upper surface exposed to the water containing groove;
a bracket including a support member located inside the main body and contacting a lower end of the watertight body and a lower end of the light transmitting cap, and a protruding member which protrudes upward of the support member and is inserted into the light transmitting cap; and
a printed circuit board fixed onto the upper surface of the protruding member and mounted with a UV LED.

3. The UV steam sterilizer of claim 2, wherein an O-ring is interposed between an inner surface of the light transmitting cap and an outer surface of the protruding member.

4. The UV steam sterilizer of claim 1, wherein the container includes:
a hollow housing forming a side wall of the containing space;
a bottom plate detachably coupled to the hollow housing and forming the bottom of the containing space, the bottom plate supporting the article and having steam passage holes for passage of the steam; and
a magnet installed on the bottom plate, wherein a hall sensor installed in the main body detects the magnet when the hollow housing coupled to the bottom plate is placed on the main body, and wherein the UV irradiation unit is controlled to irradiate the ultraviolet rays only when the hall sensor detects the magnet.

5. The UV steam sterilizer of claim 1, comprising:
a drying module built in the main body, wherein the drying module is configured to form hot air by heating outside air during operation, and then to blow the hot air to the containing space, and wherein the drying module is controlled to operate immediately after the steam heater stops.

6. The UV steam sterilizer of claim 5, wherein the drying module is controlled to operate for a preset operation time periodically when there is an input of a user for notifying that the article sterilized with the steam is present in the containing space.

7. The UV steam sterilizer of claim 5, wherein the UV irradiation unit is controlled to irradiate the ultraviolet rays when the drying module operates.

8. The UV steam sterilizer of claim 5, wherein the drying module includes:

a duct having an outside air inlet for introducing the outside air and a hot air outlet for discharging the hot air upward;

a fan and a hot air heater installed inside the duct; and a door installed in the hot air outlet to be opened by a wind pressure of the hot air and closed by its own weight; and a hood for guiding the hot air which flows out from the hot air outlet, wherein the hood is provided on the upper surface of the main body and is configured to limiting an opening angle of the door to an acute angle.

9. The UV steam sterilizer of claim 8, wherein a bottom portion of the duct located below the hot air outlet comprises a water collection groove formed more concavely downward than a bottom portion of the duct where the fan and the hot air heater are located.

10. The UV steam sterilizer of claim 9, wherein a duct drain hole is formed at the bottom of the water collection groove, and the duct drain hole communicates with a main body drain hole formed at the bottom of the main body.

\* \* \* \* \*